United States Patent
Kuo (10) Patent No.: US 8,740,490 B2
(45) Date of Patent: Jun. 3, 2014

(54) DENTIFRICE DISPENSING ELECTRICAL TOOTHBRUSH WITH INTEGRATED DISPENSING PLATFORM AND SELF SEALING SPOUT

(76) Inventor: Youti Kuo, Penfield, NY (US)

( * ) Notice: Subject to any disclaimer, the term of this patent is extended or adjusted under 35 U.S.C. 154(b) by 34 days.

(21) Appl. No.: 13/345,704

(22) Filed: Jan. 7, 2012

(65) Prior Publication Data

US 2013/0011177 A1    Jan. 10, 2013

Related U.S. Application Data (60) Provisional application No. 61/506,145, filed on Jul. 10, 2011.

(51) Int. Cl.
| | | |
|---|---|---|
| *A61C 17/34* | (2006.01) | |
| *A46B 11/02* | (2006.01) | |
| *A46B 11/00* | (2006.01) | |
| *A61C 17/22* | (2006.01) | |

(52) U.S. Cl.
CPC ........... *A61C 17/349* (2013.01); *A46B 11/0041* (2013.01); *A61C 17/227* (2013.01); *A61C 17/3436* (2013.01); *A61C 17/3445* (2013.01); *A61C 17/3454* (2013.01)
USPC ............ 401/188 R; 401/39; 401/270; 15/22.2

(58) Field of Classification Search
USPC .......................................... 401/286; 15/22.2
See application file for complete search history.

(56) References Cited

U.S. PATENT DOCUMENTS

| | | | | |
|---|---|---|---|---|
| 5,353,460 | A | * 10/1994 | Bauman | 15/22.1 |
| 6,434,773 | B1 | 8/2002 | Kuo | |
| 6,735,803 | B2 | 5/2004 | Kuo | |
| 6,902,337 | B1 | 6/2005 | Kuo | |
| 7,640,614 | B2 | * 1/2010 | Brown et al. | 15/22.1 |
| 7,789,583 | B2 | 9/2010 | Kuo | |
| 7,877,832 | B2 | 2/2011 | Reinbold | |
| 2007/0041779 | A1 | * 2/2007 | Kuo | 401/188 R |

* cited by examiner

*Primary Examiner* — David Walczak
*Assistant Examiner* — Joshua Wiljanen (57) ABSTRACT

Dentifrice dispensing electrical toothbrush comprising a driver-pump head with a dispensing platform, a replaceable brush unit and a handle having a battery and a cartridge containing dentifrice material. The replaceable brush unit includes a oscillatory brush element and a brush element having a circular or an elongated spout opening as well as a snap-on mounting bracket for fastening to the driver-pump head. The dispensing platform contains a flow channel and a self-sealing spout to prevent drying of the dentifrice material at the spout. The self-sealing spout opens and closes automatically during a pumping action. The brush element with a spout opening is detachably mounted over the spout fixed on the dispensing platform to allow for brush oscillation around the spout and receive the dentifrice material dispensed from the flow channel. Different drive mechanisms are used to impart rotary, lateral or longitudinal oscillation on a brush element in a brush unit.

6 Claims, 8 Drawing Sheets

DENTIFRICE DISPENSING ELECTRICAL TOOTHBRUSH WITH INTEGRATED DISPENSING PLATFORM AND SELF SEALING SPOUT

Claiming priority benefit of Provisional Patent Application No. 61/506,145, Filing Date: Jul. 10, 2011

BACKGROUND

It has been recognized through clinical tests that an electrical toothbrush is more effective in removing plaque and preventing gum disease than a conventional manual toothbrush. It is also well known that toothbrush bristles should be replaced on a regular basis since bristle harbor germs after a period of use. A large number of conventional disposable brushhead include a neck portion, which is a waste of material. Besides, many types of electrical toothbrush use high power vibration of neck or handle portion to achieve oscillation of brushhead, which requires high battery power. Furthermore, dispensing dentifrice material to an electrical toothbrush presents great challenges to the handicapped as an electrical toothbrush is much bulkier than a manual toothbrush for applying dentifrice material. Currently there is no electrical toothbrush commercially available that can dispense dentifrice material from its handle to brush head. For ergonomic and portability, an electrical toothbrush needs to contain and dispense dentifrice material easily with one hand to its bristles for brushing. Moreover a conventional spout for dispensing the dentifrice material requires manual capping, which is often ignored resulting in clogging and pumping failures. These shortcomings necessitate an electrical toothbrush that can dispense dentifrice material with a spout that can automatically seal itself to prevent drying of the dentifrice material.

FIELD OF INVENTION

The present invention relates to dentifrice dispensing electrical toothbrush having replaceable brush elements, an oscillation mechanism and a cartridge containing dentifrice material.

OBJECTS OF THE INVENTION

It is the objective of the present invention to provide a dentifrice dispensing electrical toothbrush using a permanent self-closing spout to dispense dentifrice material to a brush element, minimizing both the amount of disposable brush material and the battery power for the oscillation of a brush element.

PRIOR ART

U.S. Pat. No. 6,434,773 by Kuo describes a dentifrice dispensing electrical toothbrush having a flow channel to dispense dentifrice material to two replaceable oscillating brush elements. The dentifrice material is pumped from a cartridge to a spout opening at the base of one brush element. The two brush elements are detachably mounted on two posts on the platform of the brushhead neck through the use of a snap-on mounting bracket. The oscillating motion of the brush elements is imparted by the engagement of notches at the bottom of the brush elements to an end-cap which is attached to a shaft driven by a motor. Although the two brush elements are replaceable, their mounting on two posts which are fixed on the neck platform requires significant pulling force to detach them from the posts, not an easy task for general users. Moreover, the shaft's end-cap is situated in a restricted recess area between two posts, which is not accessible for cleaning as needed between replacements of the brush elements. Additionally, the spout opening is not self-closing, therefore, exposing the dentifrice material to ambient air causing drying of the dentifrice material and resulting in clogging of the flow channel leading to pumping failures.

U.S. Pat. No. 6,735,803 by Kuo provides an electrical dentifrice dispensing ( ) having a replaceable bristle unit consisting a rotary brush element and a stationary brush element which has a spout opening for the flow of dentifrice material. A linkage is used to convert the rotation of the drive shaft to a planar oscillation that enables a compact drive head configuration. The dispensing of dentifrice material is accomplished by using a rotary solenoid for actuating an internal button that applies pumping pressure to the dentifrice material. As a benefit to arthritis suffers, no external squeezing action is involved. Again, the ( ) provides neither open access to the shaft engagement area for cleaning nor self-closing spout for preventing drying of dentifrice material.

To resolve brushhead cleaning problem at replacement, U.S. Pat. No. 6,902,337 by Kuo describes a dentifrice dispensing electrical toothbrush using a replaceable dual-channel brush element. The dual-channel brush element has a first channel for housing a drive shaft for bristle oscillation and a second channel for dispensing the dentifrice material. The brush element is mounted on the dual-channel connector of the brush handle, which contains a drive mechanism and a pumping mechanism that dispenses dentifrice material from a cartridge in the handle. No shaft cleaning is needed at the replacement of the brushhead but the whole dual-channel brushhead is discarded at replacement that is an expensive waste of material.

U.S. Pat. No. 7,789,583 by Kuo describes manual and electrical pump ( )es using a slit valve for preventing drying. The slit valve, which is made of rubber or elastomeric material, prevents backflow and drying of the dentifrice material at the spout opening. However, the inclusion of the rubber slit-valve in otherwise plastic dual channel brushhead makes the whole bulky disposable brushhead a non-recyclable item.

To impart vibration to a brushhead without using a rotary brush element, U.S. Pat. No. 7,877,832 by Reinbold describes a powered ( ) comprising a handle containing a motor and a power supply, and a brush element including a neck which is flexibly and resiliently connected to the handle. The motor and a transmission means are pivotally mounted within the handle and use the vibration of the handle to oscillate the brush element-and-neck. The method has disadvantages of replacing the whole brush element-and-neck and requiring extra motor power to vibrate the handle in order to oscillate the brush element-and-neck. It is a waste of neck material and battery power.

Therefore, it is desirable to have an electrical toothbrush that has a slit valve mechanism for preventing drying of dentifrice material and not part of a disposal brushhead. It is desirable to use a disposable brush unit without having a conventional neck portion. It is also desirable to impart oscillation of brush elements without causing vibration to the neck and handle of an electrical toothbrush to save battery power. Furthermore, it is desirable to have common brush unit and driver-pump head configurations for different types of brush oscillation.

SUMMARY OF THE INVENTION

A dentifrice dispensing electrical toothbrush is provided with a driver-pump head having an extended dispensing platform attached with a slit spout, a replaceable brush unit and a refillable cartridge for storing dentifrice material. A replaceable brush unit consists of only brush elements and a mounting bracket without a conventional neck portion. The driver-pump head including the dispensing platform and the slit spout is for repeated permanent uses. The brush unit is equipped with snap-on fastening arms for conveniently attached to and detached from the driver-pump head. A brush element having a spout opening is mounted over the slit spout to receive the dentifrice material from the flow channel in the dispensing platform. The slit spout is self-sealing to prevent drying of the dentifrice material at the spout. An elastic compressible button is used to apply pumping pressure. The slit spout is forced to open by the exiting dentifrice material and to close by the vacuum force created when the pumping pressure is released. The vacuum force also causes the piston in the cartridge advance to push the dentifrice material into the pumping chamber through a one-way check valve in the pump head.

Various configurations of brush unit and drive mechanism for the oscillation of brush elements are given. For a brush unit having two rotary brush elements with one having circular spout opening, drive notches of both brush elements are directly engaged with a drive shaft undergoing limited angular oscillation. For a brush unit having one rotary brush element and one translational element having an elongated spout opening, the longitudinal oscillation of the translational element is driven by a linkage connected to the rotary brush element. For a brush unit having a single unitary brush element with a spout opening elongated in lateral direction, the lateral oscillation of the brush element is guided by parallel side guides on the mounting bracket for free sliding support. For a brush unit having a single unitary brush element with a longitudinal spout opening, the longitudinal oscillation is achieved by a drive mechanism using bevel gears with a biased wheel and a linkage bar to cause axial oscillation of the drive shaft to impart oscillation to the unitary brush element. In all these brush unit and drive configurations, only the brush elements are oscillated while the mounting bracket and the handle are non-oscillatory to save battery power.

BRIEF DESCRIPTION OF THE DRAWINGS

FIG. 1b is a front section view of the assembled electrical pump toothbrush of FIG. 1a.

FIG. 4c is a perspective view of a dispensing platform for the mounting bracket of FIG. 4b and the unitary brush element of FIG. 4a.

FIG. 6c is a perspective view of a dispensing platform for the mounting bracket of FIG. 6b and the unitary brush element of FIG. 6a.

FIG. 9a is a front section view of a brush unit having fastening pushbuttons.

FIG. 9b is a side cross-section of the brush unit of FIG. 9a.

FIG. 9c is a side cross-section of a driver-pump head for the brush unit of FIG. 9a.

FIG. 9e shows the mounting of the brush unit of FIG. 9b on the driver-pump of FIG. 9c.

DESCRIPTIONS OF THE INVENTION

Figure 1A:
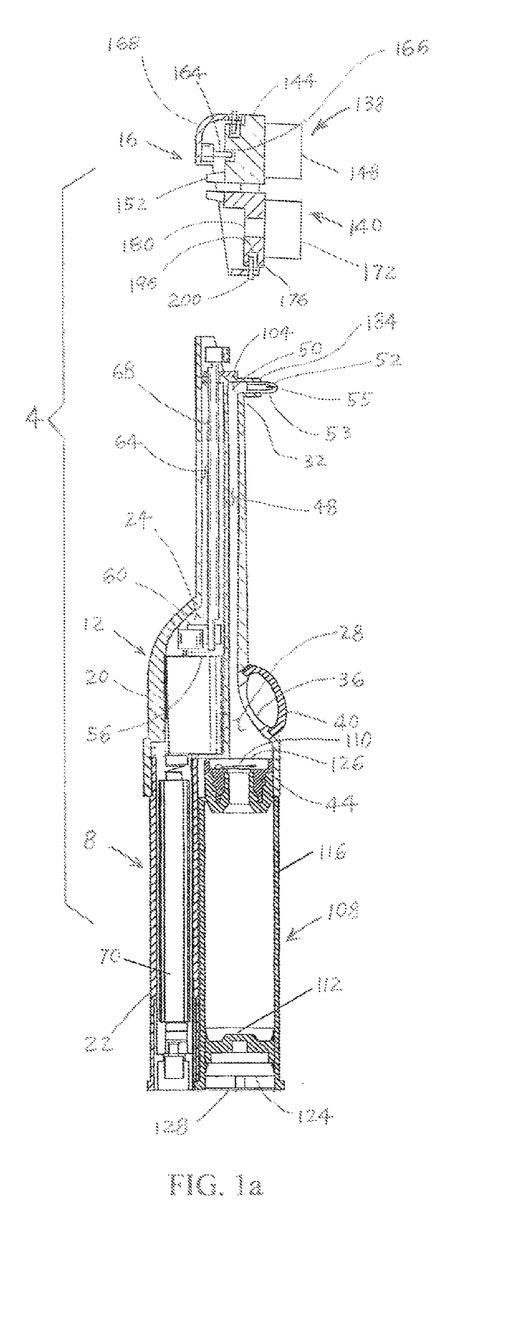
FIG. 1a is a front section view of an unassembled electrical pump toothbrush having a handle, a driver-pump head and a brush unit.
Figure 1B:
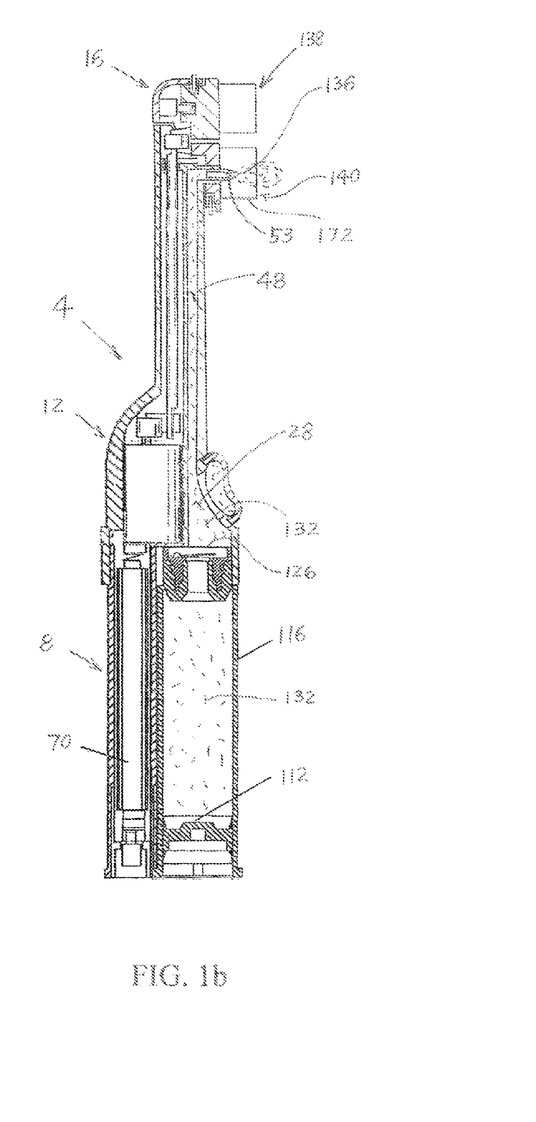

Throughout the following detailed descriptions, same reference numerals refer to the same elements in all figures.
Driver-Pump Head The structure and function of the dentifrice dispensing electrical toothbrush of the present invention are described in details as follows. As shown in FIGS. 1a, 1b, a dentifrice dispensing electrical toothbrush 4 of present invention includes handle 8, driver-pump head 12 and brush unit 16. FIG. 1a shows dentifrice dispensing electrical toothbrush 4 un-assembled with brush unit 16 being detached from driver-pump head 12. Handle 8 includes housing wall 22, battery 70, and cartridge 108 which is a reservoir storing dentifrice material.

Figure 2:
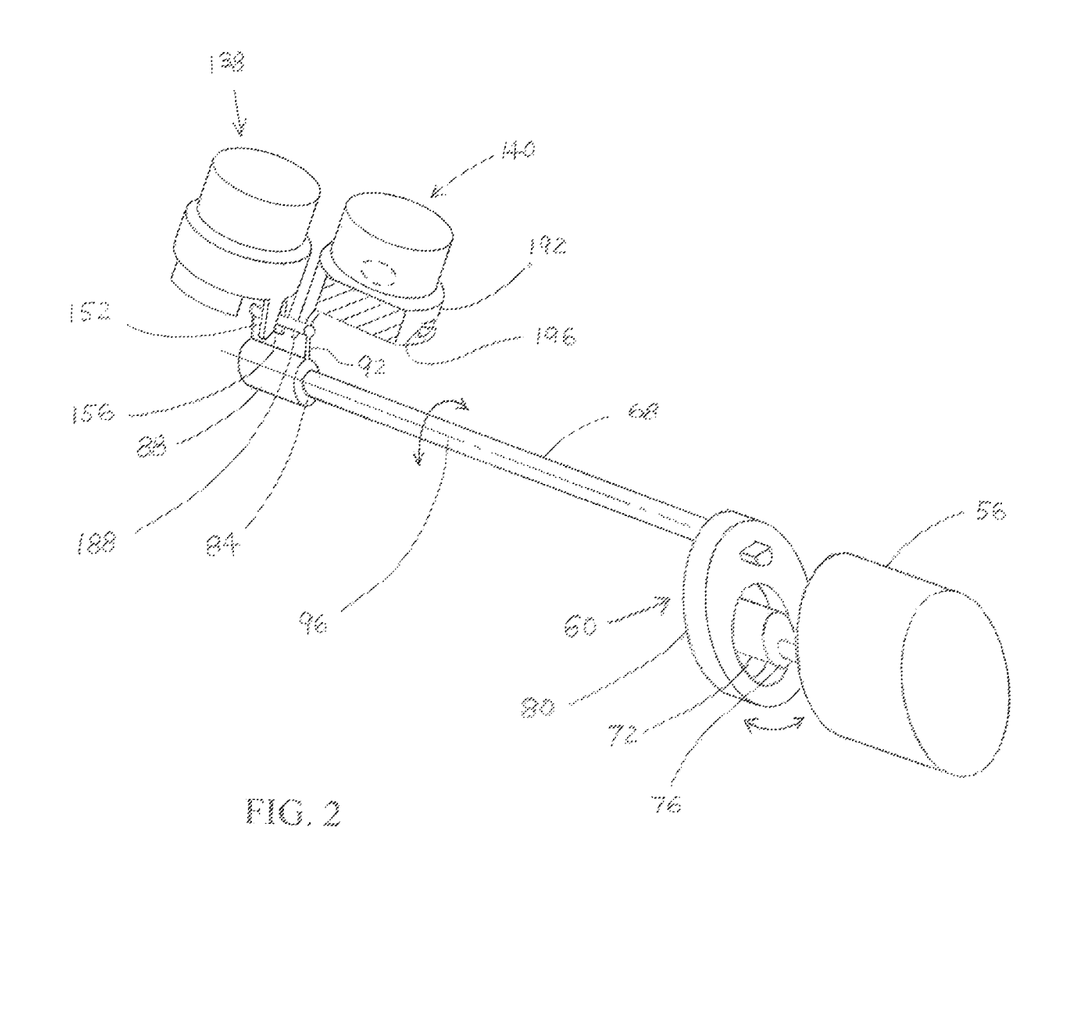
FIG. 2 is a perspective view of a drive shaft with an oval-shaped cam.

Driver-Pump head 12 includes side wall 20, driving chamber 24, and pumping chamber 28. Pumping chamber 28 includes side opening 36 attached with actuator 40, inlet connector 44 and dispensing platform 32, which has flow channel 48 attached with spout 52. Both inlet connector 44 and dispensing platform 32 are supported by sidewall 20. Driving chamber 24 includes motor 56, cam assembly 60 and a shaft channel 64 including a drive shaft 68. The motor is powered by battery 70 positioned within the handle. Referring to FIG. 2, drive shaft 68 and motor 56 are connected by cam assembly 60, which imparts an oscillating motion to the drive shaft. Motor drives bias wheel 72, which is connected to motor output shaft 76. An oval-shaped cam 80 is connected to top end 84 of drive shaft 68. End cap 88 is attached to top end 84 of the drive shaft with tab 92 extending radially outward from the central longitudinal axis 96 of the drive shaft. When connected to the drive shaft as shown in FIG. 2, tab 92 oscillates with the drive shaft and imparts oscillating motion to brush elements 138 and 140. The off-center position of a biased wheel controls the amplitude of the angular oscillation of the drive shaft, which in turn limits the amplitude of the rotary oscillation of the brush element being driven. Referring to FIG. 1a, bearing 104 is used for supporting drive shaft and for preventing cleaning water into the shaft channel 64. Dentifrice cartridge 108 having piston 112 is attached to inlet connector 44. On FIG. 1a, cartridge 108 includes cylindrical tube 116 and piston 112. Cylindrical tube 116 has interior threads on annular wall extension at top opening end 126. Piston 112 having flexible upper annular rim 120 and lower annular rim 124 is inserted into cylindrical tube 116 through bottom opening end 128 of the cartridge to provide slidable sealing of the dentifrice material inside the cartridge. Each component and its function will be further described in detail in the following sections.

Pumping Action

FIG. 1b shows assembled dentifrice dispensing electrical toothbrush 4 having brush unit 16 mounted on driver-pump head 12. Dentifrice material 132 is pumped from pumping chamber 28, through flow channel 48 and spout exit 136, to bristles 172 of brush element 140. A pumping force is applied to the pumping chamber by depressing on actuator 40. In a preferred embodiment, actuator 40 is an elastic compressible button and its location in the driver-pump head with respect to the handle is convenient to apply the pumping pressure in one hand operation. When the pumping force is released, the elastic compressible button returns to its original position automatically due to the resiliency of its rubber material. The vacuum force created inside pumping chamber 28 by releasing of the actuator causes dentifrice material 132 to flow from cartridge 108 through one way check valve 110 and into the pumping chamber to replace the dentifrice material removed from the pumping chamber. The exiting of dentifrice material from cartridge 108 causes corresponding advancement of piston 112 toward the top opening 126 of the cartridge. As shown in FIG. 1b, the flow channel 48 provides the flow path for dentifrice material from the pumping chamber 28 to the brush element 140.

Dispensing Platform and Slit Spout

In the present invention a slit spout is fixed to the dispensing platform, which is an extended portion of the driver-pump head. FIG. 1b shows dispensing platform having flow channel 48 extended from the pumping chamber 28 and outlet opening 50. In a preferred embodiment spout 52 is of slit configuration. Slit spout 52 has tubular wall 53 with cross-slits 55 at its apex. A slit spout is preferably made of thermoplastic elastomer material for resiliency by dip or injection molding and the cross slits are formed by slicing action of a sharp blade. A slit-spout has multiple flappers forming a normally closed dome-shaped surface when the cavity is empty or not under pressure. Each flapper is a curved triangular valve segment extending from tubular wall with tip of each valve segment intercepting at the apex when the slit spout is closed. Each flapper segment can be bent outward like a cantilever beam such that slit spout 52 is at open state at exit 136 as shown in FIG. 2b. The slit-spout is forced to open by exiting dentifrice material under the pumping pressure when the elastic compressible button 40 is depressed as shown in FIG. 1b. The slit spout closes after the elastic button is released. The slit length, wall thickness and the elastic modulus of the spout material are designed to ensure closing of the slit spout by the resiliency and the vacuum force created when the pumping force is released. Slit spout is attached to the outlet opening 50 by adhesive means. Alternatively a slit valve may be designed with a flexible flange (not shown) at its base for insertion into the flow channel 48 where the flange is latched beneath the outlet opening 50 for securing the slit spout in place.

Brush Unit Assembly

A brush unit of the present invention is detachably mounted on the dispensing platform 32. Brush unit 16 as shown in FIG. 1a includes two rotary brush elements 138 and 140. First rotary brush element has base 144 having its frontside attached with bristles and its backside attached with notch extension 152 with notch 156 (shown in FIG. 2). Referring to FIG. 1a, the center of the backside also has a recess 166 which is shaped to mate with post 164 on the mounting bracket 168 for free rotation. In addition to bristles, base 56 of second brush element 140 has spout opening 180 for detachably mounting over outlet opening wall 184 on the dispensing platform 32 to receive the dentifrice material dispensed from the slit spout. Notches 156, 188 are mounted on top of tab 92. A limited angular oscillating motion of tab causes brush elements 138 and 140 to oscillate freely around post 164 and outlet opening wall 184, respectively. Furthermore, as will be shown in later sections, sidewall of each brush element has groove for accommodating a retention pin on the mounting bracket for maintaining the height of the brush element from the dispensing platform for free oscillation. The width of each groove is sufficient to allow for the range of the angular oscillation of each brush element.

For fastening the bristles elements to the dispensing platform, a mounting bracket is used. Detailed descriptions of a mounting bracket of the present invention will be given in later sections.

Rotary and Translational Brush Elements

Figure 3:
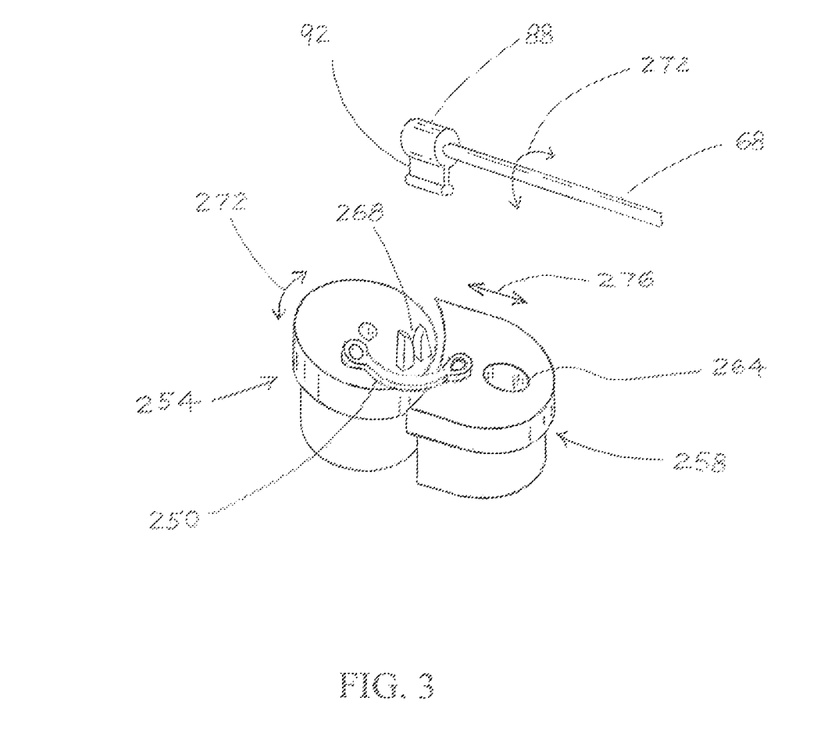
FIG. 3 shows a drive shaft and a bottom view of a linkage between a rotary brush element and a translational brush element having longitudinal spout opening.

In addition to the configuration for the oscillation of two rotary brush elements, the driver-pump head having a dispensing platform and a slit spout is applicable to a brush unit having a rotary brush element and a translational brush element. FIG. 3, without including a mounting bracket, shows drive shaft 68 and a bottom view of linkage 250 between rotary brush element 254 having notch 268, and translational brush element 258 having spout opening 264 elongated in the longitudinal direction, which is aligned in the axial direction of drive shaft 68. When tab 92 of end cap 88 of the drive shaft 68 is engaged with the notch 268 of the rotary brush element 254, the angular oscillation 272 of the drive shaft imparts linear oscillation 276 of the translational brush element 258. As the translational brush element oscillate, the spout opening moves up and down with respect to a slit spout which is fixed to a dispensing platform as described in FIG. 1a.

Unitary Brush Unit with Lateral Spout Opening

The driver-pump head having a dispensing platform and a slit spout is also applicable to a unitary brush element structure, which has one base combining the features of drive notch and spout opening in one brush element. In a unitary brush element configuration, the oscillation of the brush element can be either in lateral or in longitudinal direction as will be described in the following sections.

Figure 4A:
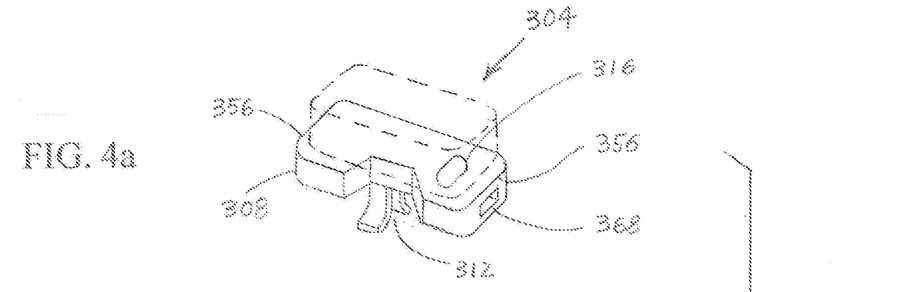
FIG. 4a is a perspective view of a unitary brush element having lateral spout opening and a notch under the base of the brush element.
Figure 4B:
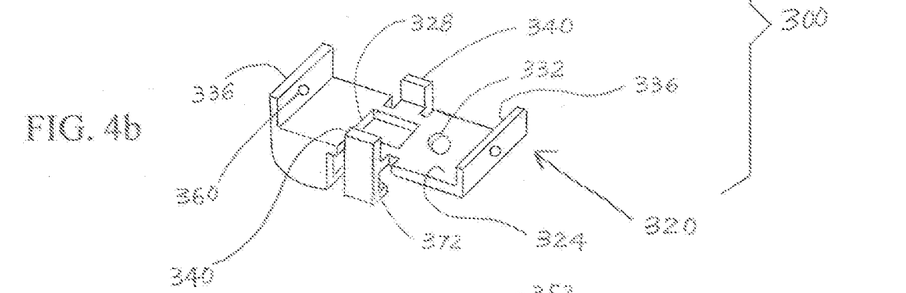
FIG. 4b is a perspective view of a mounting bracket for the unitary brush element of FIG. 4a showing parallel guides and fastening arms.
Figure 4C:
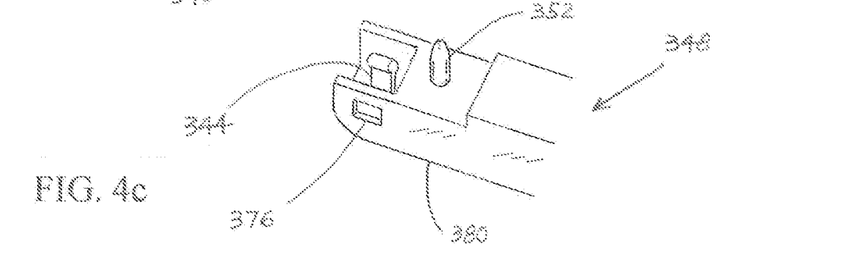

FIGS. 4a, 4b, 4c show un-assembled brush unit 300 detached from dispensing platform 348. The structure of the unitary brush unit 300 is for oscillating in the lateral direction, which is perpendicular to a drive shaft as described previously. FIG. 4a shows unitary brush element 304 having notch 312 positioned under and at the center of base 308 and a lateral spout opening 316 elongated perpendicular direction to a drive shaft that is engaged with notch 312. Mounting bracket 320 for unitary brush element 304 is shown in FIG.

Figure 4D:
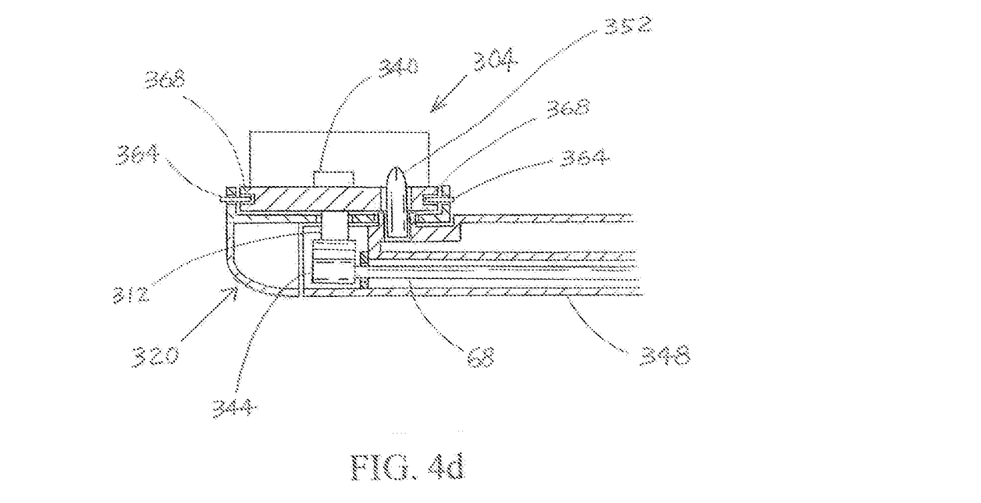
FIG. 4d is a front section view of the mounting of the unitary brush element and the mounting bracket on the dispensing platform of FIGS. 4a, 4b and 4c.

4b. The mounting bracket 320 comprises base 324 having notch opening 328 and spout opening 332, two parallel side guides 336 and a pair of fastening arms 340. The notch opening 328 is for inserting notch 312 of the unitary brush element 316 through base 324 to engage with the end cap 344 of the dispensing platform 348 as shown in FIG. 4c. The spout opening 332 is for inserting slit spout 352 through base 324 and through the elongated spout opening 316 of the brush element as shown in FIG. 4d, which shows the mounting of the unitary brush element 304 and the mounting bracket 320 on the dispensing platform 348. The parallel side guides 336 are for sliding-fit with sidewalls 356 of the brush element 304 for free lateral oscillation. Side guide 336 has pinhole 360 for accommodating a retention pin 364, which is inserted into groove 368 on sidewall 356 of brush element 304. The engagement of the pair of retention pins 364 and grooves 368, as shown in FIG. 4d is for maintaining free lateral oscillation of the brush element 304 on top of the mounting bracket 320 by drive shaft 68.

Mounting Bracket and Fastening Arms

The use of fastening arms as described in U.S. Pat. No. 6,434,773 is applicable to the mounting bracket of the present invention. It is briefly described as follows. Referring to FIGS. 4a, 4b and 4c, mounting bracket 320 for the brush element 304 is attachable to and detachable from the dispensing platform 348 by squeezing on upper ends of a pair of fastening arms 340 on opposite sidewalls of the mounting bracket 320. The lower end of each fastening arm 340 has an inward protruding rib 372 which detachably engages a recess 376 on sidewall 380 of the dispensing platform 348. The fastening arms are designed to function as a pair of cantilever beams in a manner inward deflections of their upper ends toward each other causes outward deflections of their lower ends, such that the ribs are detached from the dispensing platform.

Figure 5A:
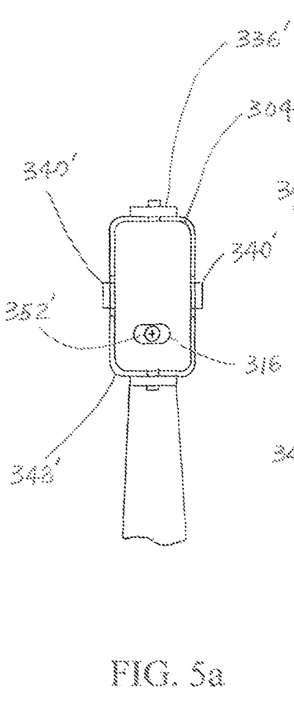
FIG. 5a is a top view of a unitary brush element having lateral spout opening at the middle position with respect to the spout.
Figure 5B:
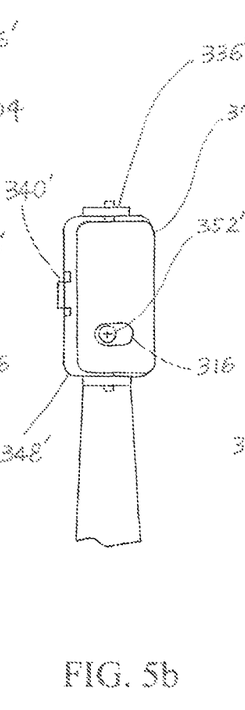
FIG. 5b is a top view of the unitary brush element of FIG. 5a with the lateral spout opening moved to the right of the spout.
Figure 5C:
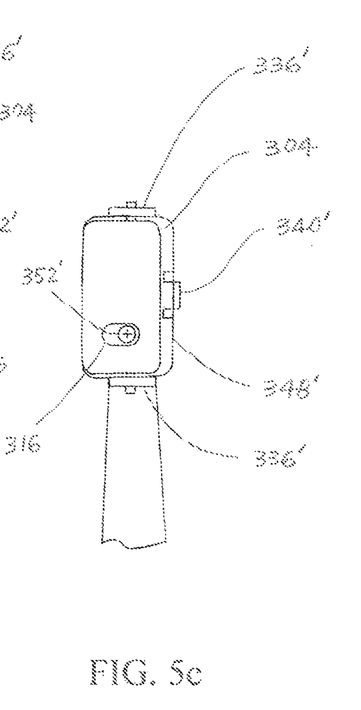
FIG. 5c is a top view of the unitary brush element of FIG. 5a with the lateral spout opening moved to the left of the slit spout.
Figure 5D:
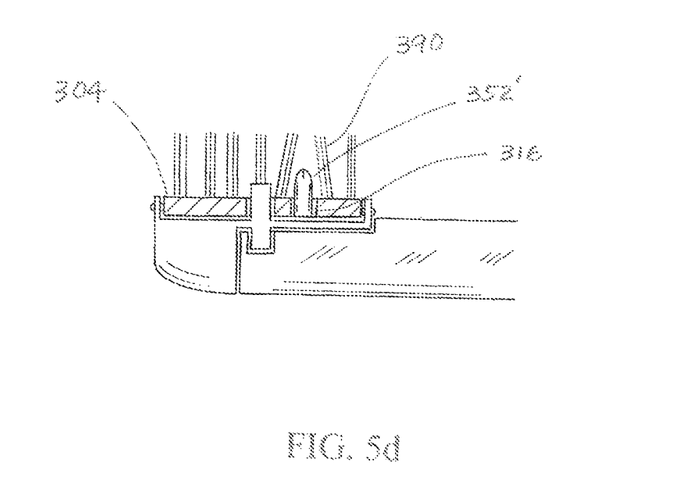
FIG. 5d is a front section view of the unitary brush element of FIG. 5a showing angled bristles surrounding the spout opening.

With unitary brush element and the mounting bracket latched on the dispensing platform, FIGS. 5a, 5b and 5c show different lateral positions of the unitary brush element 304 with respect to side guides 336', fastening arms 340' and slit spout 352' in the dispensing platform 348'. Specifically, FIGS. 5a, 5b and 5c show the spout opening 316 at the middle position, moved to the right and to the left of the slit spout' 352', respectively, when the brush element 308 is in oscillation motion. In order for the space above the spout area to have bristle coverage or to reduce the void, tufts of bristles around the spout opening are tilted toward the spout opening. FIG. 5d shows angled tufts 390 of bristles in brush element 304 surrounding the spout opening 316 being tilted toward the center of the spout opening 316.

Unitary Oscillatory Brush Element

Figure 6A:
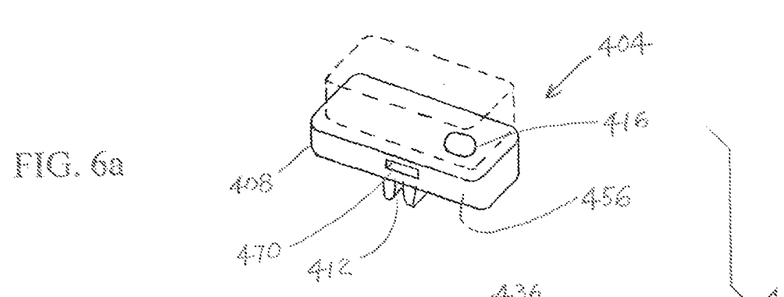
FIG. 6a is a perspective view of a unitary brush element having longitudinal spout opening and a notch under the base of the brush element.
Figure 6B:
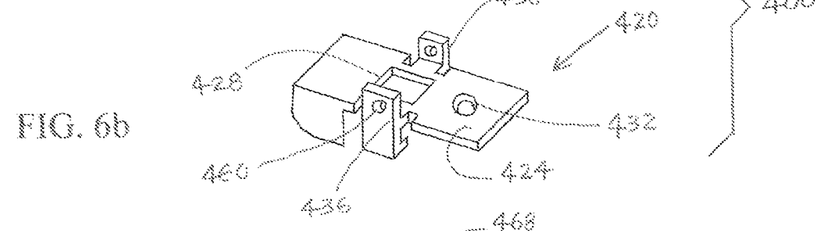
FIG. 6b is a perspective view of a mounting bracket for the unitary brush element of FIG. 6a showing parallel guides and fastening arms.
Figure 6C:
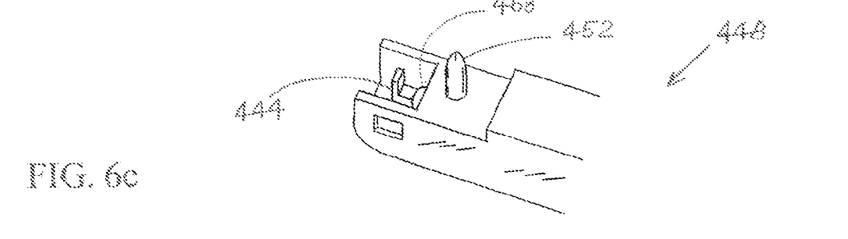
Figure 6D:
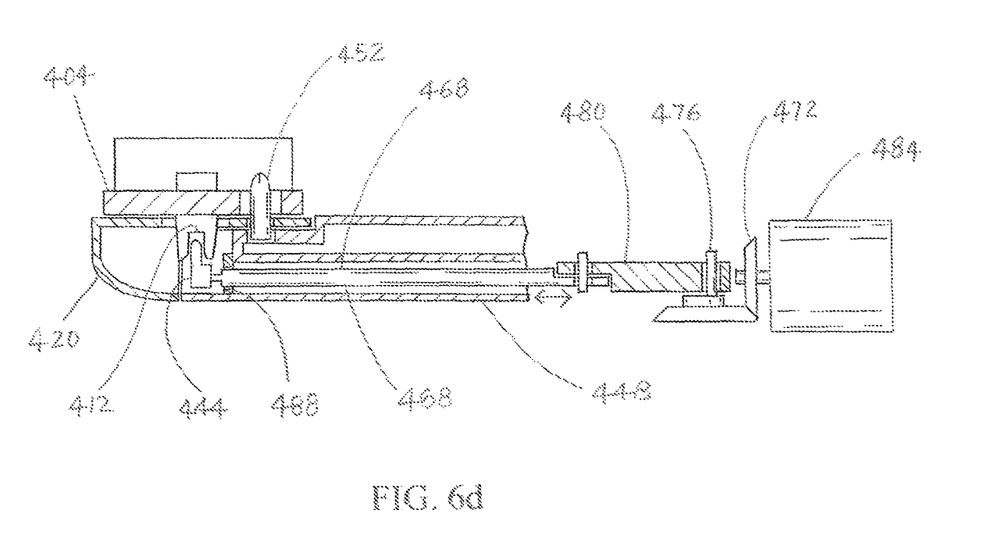
FIG. 6d is a front section view of the mounting of the unitary brush element and the mounting bracket on the dispensing platform of FIGS. 6a, 6b and 6c.

In another unitary brush unit configuration, a brush element for longitudinal oscillation has its spout opening elongated in the longitudinal direction of the brush element. FIGS. 6a, b, c and FIGS. 6a, 6b, 6c show un-assembled unitary brush unit 400 detached from dispensing platform 448. The structure of the unitary brush unit 400 is for oscillating in the longitudinal direction of the brush element 404. FIG. 6a shows unitary brush element 404 having notch 412 under its base 408 and a longitudinal spout opening 416, which is an elongated slot oriented in the axial direction of a drive shaft that is engaged with notch 412. Mounting bracket 420 for the unitary brush element 404 is shown in FIG. 6b. Mounting bracket 420 comprises base 424 having notch opening 428, spout opening 432, and two parallel side guides 436 which function as fastening arms. Similarly, notch opening 428 is for inserting notch 412 of the unitary brush element 404 through base 424 to engage with the top end 444 of drive shaft 468. The top end 444 is shaped as a bent tab as shown in FIG. 6c to engage with notch 412 to impart notch oscillation. The spout opening 432 is for inserting slit spout 452 through the bracket base 424 and the elongated spout opening 416 of the brush element 404 as shown in FIG. 6d. The parallel side guides 436 are for sliding-fit with the sidewalls 456 of brush element 404 for guiding free longitudinal oscillation. Side guide 436 has pinhole 460 for accommodating a retention pin (not shown), which is inserted into groove 470 on sidewall 456 of the brush element 404. The engagement of the pair of retention pins and grooves is for maintaining free lateral oscillation of the brush element on top of the mounting bracket. Mounting bracket 420 for brush element 404 is attachable to and detachable from the dispensing platform 448 by squeezing on upper ends of fastening arms 436 on opposite sidewalls of the mounting bracket 420, whose functions have been described previously.

In one embodiment, the longitudinal oscillation of drive shaft 468 is achieved by a means of bevel gears 472, biased wheel 476 and linkage mechanism 480 in connection with motor 484 as shown in FIG. 6d. When motor 484 is energized, the change of rotation of bevel gears 472 causes the biased wheel to swing the linkage bar that in turn causes the drive shaft 468 to move forward and backward in oscillation. The reciprocating motion of the drive shaft causes the brush element 404 to oscillate in longitudinal direction accordingly. The drive shaft is being supported at the top end with bearing 488 preventing cleaning water or foreign media getting into the shaft channel. The bearing provides free sliding support to the shaft without transmitting shaft oscillation to the shaft channel, the driving chamber and the handle of an electrical toothbrush of the present invention.

Figure 7:
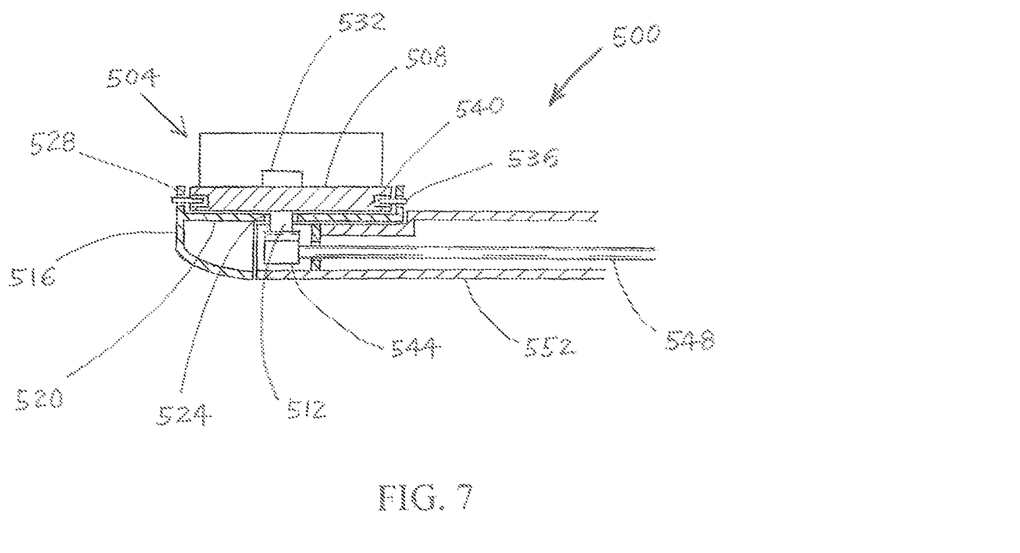
FIG. 7 is a front section view of an electrical toothbrush having a lateral oscillation brush element.

The structure of a unitary brush unit and its associated drive mechanism as described above are applicable to an electrical toothbrush. An electrical toothbrush does not contain dentifrice material. FIG. 7 shows an electrical toothbrush 500 of the present invention having a lateral oscillation brush element 504. The brush element 504 has notch 512 under its brush base 508 with notch orientation in the longitudinal direction of the brush element 504. Mounting bracket 516 has bracket base 520 having a notch opening 524, two parallel side guides 528 and a pair of fastening arms 532. The parallel side guides are for sliding-fit with the sidewalls of the brush element for free lateral oscillation. Each side guide has a pinhole for accommodating retention pin 536, which is inserted into groove 540 on a sidewall of the brush element. The notch opening 524 is for inserting notch 512 of the brush element 504 through bracket base 520 to engage with end cap 544 of drive shaft 548. The drive shaft is contained inside neck having cylindrical wall 552, which is extended from the handle. The angular oscillation of the drive shaft as generated by a cam and biased wheel mechanism as described previously imparts lateral oscillation of the brush element 504 without causing the vibration of the neck and handle of an electrical toothbrush of the present invention.

Figure 8:
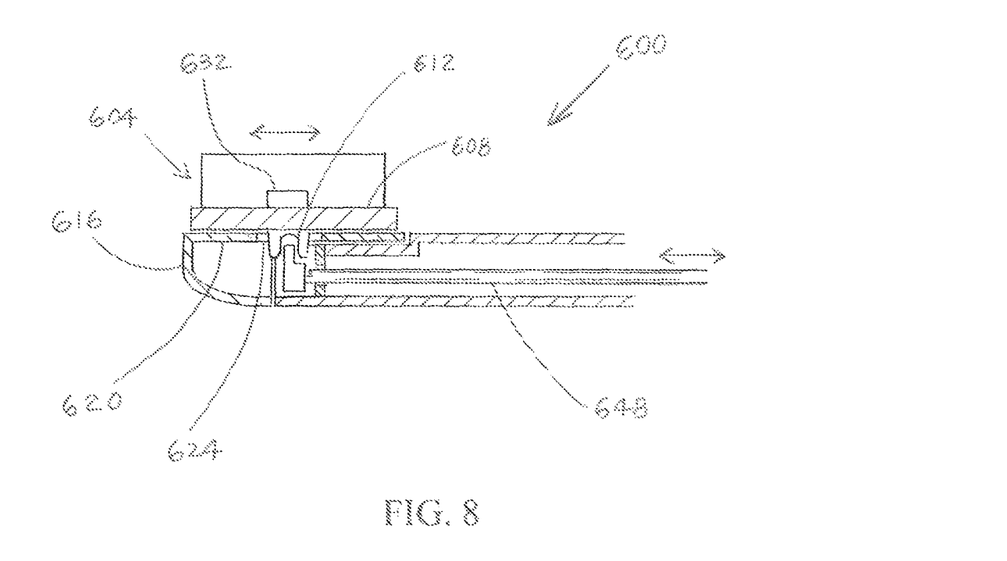
FIG. 8 is a front section view of an electrical toothbrush having a longitudinal oscillation brush element.

Furthermore, FIG. 8 shows an electrical toothbrush 600 having a longitudinal oscillation brush element 604. The brush element has notch 612 under its base 608 with notch orientation in the lateral direction of the brush element. Mounting bracket 616 has base 620 having notch opening 624, two parallel side guides 632, which also function as a pair of fastening arms. The parallel side guides are for sliding-fit with the sidewalls of the brush element for guiding free longitudinal oscillation. The reciprocating oscillation of the drive shaft 648 as driven by bevel gears, with a biased wheel and linkage mechanism similar to that previously described in FIG. 6d, imparts longitudinal oscillation of the brush element 604 without causing the vibration of the neck and handle of an electrical toothbrush of the present invention.

Brush Unit with Pushbuttons

In the preceding brush unit configurations, a brush unit is equipped with a pair of fastening arms attached on the opposite sidewalls of its support bracket. In another embodiment of the present invention, a brush unit is mounted onto a dispensing platform by means of a pair of pushbuttons.

Figures 9A, 9B, 9C, 9E:
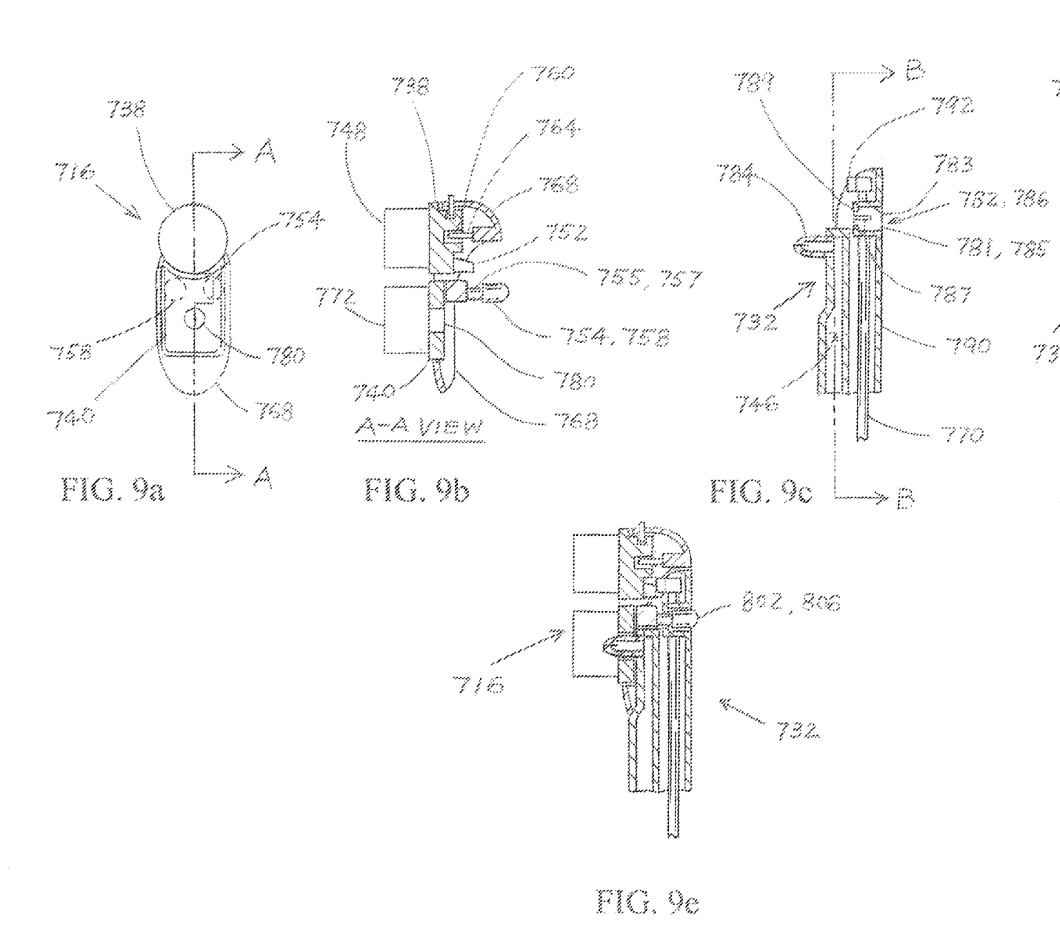
Figure 9D:
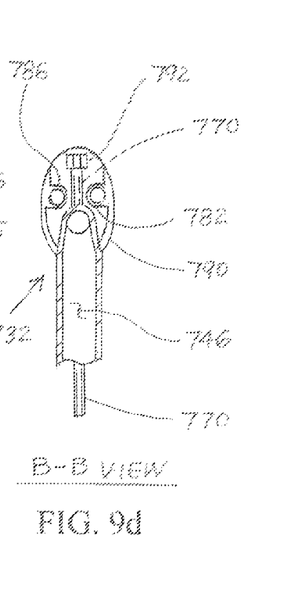
FIG. 9d is a front cross-section of the driver-pump head of FIG. 9c.

For simplicity of descriptions, a brush unit having a rotary and a stationary brush element is illustrated in FIGS. 9a and 9b. Brush unit 716 as shown in FIGS. 9a, 9b includes rotary brush elements 738 and stationary brush element 740. Rotary brush element 738 has its front attached with bristles 748 and its backside attached with notch extensions 752. The center of the backside has a recess 760 which is shaped to mate with post 764 on support bracket 768 for free rotation. In addition to bristles 772, brush element 740 has spout opening 780 for detachably mounting over spout 784 on the dispensing platform 732, which is shown in FIGS. 9c, 9d, to receive the dentifrice material dispensed from the slit spout.

The function and configuration of the dispensing platform 732 are similar to that described previously with its flow channel 746 being in communication with a dentifrice cartridge and shaft 770 being driven by a motor in a handle as shown in FIGS. 1a, 1b. Notch extensions 752 forms notches mounted on top of tab 792, which is attached to the top end of drive shaft 770. A limited angular oscillating motion of tab 792 causes brush element 738 to oscillate freely around post 764. For fastening brush unit 716 onto dispensing platform 732, the brush unit has a pair of pushbutton posts 754, 758 attached to the backside of support bracket 768. The pushbutton posts, each having a pushbutton head, are positioned to mate with receptacles 782, 786, which are attached to shaft channel wall 790 of dispensing platform 732. The receptacles are positioned on each side of shaft 770. Specifically, receptacle 782 has opening 785, annular cantilever beams 783 with split gaps 787 and ribs 789 at their distal ends. When brush unit 716 is mounted on dispensing platform 732 as shown in FIG. 9e, pushbutton posts are inserted into receptacles 782, 786 by deflecting cantilever beams to expose the heads 802, 806 of pushbutton posts 754, 758 through openings 781, 785 such that the ribs spring back to latch on retention neck 755, 757 of pushbutton posts 754, 758. In practice, the length of the cantilever beams may be shortened and the protrusion of the retention ribs may be minimized for providing effective interference for the insertion of the pushbutton posts to ensure locking of each pushbutton on the receptacle when fully engaged. The protrusion of each pushbutton head from the outer surface of the dispensing platform wall exceeds the thickness of the ribs of the receptacle such that full depression of the pushbutton head onto the receptacle opening can deflect the ribs away from the path of the detention neck to allow detachment of the brush unit from the dispensing platform. To detach the brush unit from the dispensing platform, both heads of the pushbutton posts can be pressed out of the receptacles by the thumb of one hand. The features of the receptacle configuration can be molded onto the support wall of the dispensing platform by injection molding. Similarly, the features of the pushbutton posts can be molded onto the support bracket of the brush unit by injection molding techniques. Although the above fastening features are illustrated on a dentifrice dispensing electrical toothbrush, the same fastening features are applicable to a brush unit of an electrical toothbrush. In application to an electrical toothbrush, a detachable brush unit can be molded with pushbutton posts and heads to mate with the receptacles on the shaft channel wall which are extended from the handle of the electrical toothbrush.

The invention has been described in detail with reference to preferred embodiments thereof. However, it is understood that variations and modifications can be effected within the spirit and scope of the invention.

I claim:

1. A dentifrice dispensing electrical toothbrush comprising: a. a handle having a reservoir containing a dentifrice material and a driver-pump head including: i. a pumping chamber having a side opening attached with an actuator, ii. a driving chamber including a drive shaft and a means of imparting oscillatory motion to the drive shaft, iii. a dispensing platform attached with a slit spout receiving dentifrice material from said reservoir when the actuator is depressed, said dispensing platform being an extended portion of said driver-pump head, b. a replaceable brush unit attached to said dispensing platform, said brush unit comprising: i. a first brush element having a first base attached with bristles, said first base having a notch driven in oscillatory motion by said drive shaft, ii. a second brush element having a second base attached with bristles, said second base having a spout opening for inserting with said slit spout to receive the dentifrice material dispensed from said slit spout, and said brush unit being detachable from said dispensing platform while the dentifrice material is being enclosed inside said slit spout.

2. The dentifrice dispensing electrical toothbrush of claim 1 wherein said first base and said second base are in one base forming a unitary brush element and said spout opening being an elongated slot oriented in the perpendicular direction to the drive shaft and the unitary base being driven in oscillating motion in the same perpendicular direction.

3. The dentifrice dispensing electrical toothbrush of claim 1 wherein said first base and said second base are in one base forming a unitary brush element and said spout opening being an elongated slot oriented in the axial direction of the drive shaft and the unitary base being driven in oscillating motion in the same axial direction.

4. The dentifrice dispensing electrical toothbrush of claim 1 wherein bristles surrounding said spout opening being tilted toward the center of said spout opening.

5. The dentifrice dispensing electrical toothbrush of claim 1 wherein said slit spout dispenses said dentifrice material when said actuator is depressed while said brush unit being detached from said dispensing platform.

6. The dentifrice dispensing electrical toothbrush of claim 1 wherein said slit spout dispenses said dentifrice material when said actuator is depressed while said second brush element being driven by said first brush element to oscillate with respect to said slit spout.

* * * * *